United States Patent [19]

Lynn et al.

[11] Patent Number: 5,215,537
[45] Date of Patent: Jun. 1, 1993

[54] SEPTUM FOR A BLUNT CANNULA

[76] Inventors: Lawrence A. Lynn, 1275 Olentangy River Rd., Ste. 202, Columbus, Ohio 43212; James R. Longacre, 3621 Littledale Rd., Kensington, Md. 20895

[21] Appl. No.: 581,697

[22] Filed: Sep. 13, 1990

[51] Int. Cl.⁵ ............................................. A61M 5/00
[52] U.S. Cl. ................................... 604/244; 604/256; 215/249
[58] Field of Search ..................... 604/86–88, 604/93, 99, 167, 169, 175, 201, 244, 256, 411, 415, 905; 128/764; 215/247, 249, DIG. 3

[56] References Cited

U.S. PATENT DOCUMENTS

| | | | |
|---|---|---|---|
| 1,180,665 | 4/1916 | McElroy | 604/415 |
| 2,876,775 | 3/1959 | Barr et al. | 215/DIG. 3 |
| 2,896,629 | 7/1959 | Warr | 604/99 |
| 3,364,890 | 1/1968 | Anderson | 215/DIG. 3 |
| 4,163,500 | 8/1979 | Gunne et al. | 215/247 |
| 4,496,349 | 1/1985 | Cosentino | 604/175 |

Primary Examiner—John D. Yasko
Assistant Examiner—Anthony Gutowski
Attorney, Agent, or Firm—Longacre & White

[57] ABSTRACT

An elastomeric member for occluding a medical terminal such as a junction terminal to provide a seal and penetratable to establish fluid connection by a blunt needle or cannula in which improved security against passage of contamination is provided. The needle or cannula preferably passes through a perforated passage. The passage can have at least two portions, one having a slit for normally sealing tightly in the absence of a cannula or needle and the other having a bore communicating with the slit and closely conforming to the cannula surface. Other sealing arrangements are detailed.

3 Claims, 4 Drawing Sheets

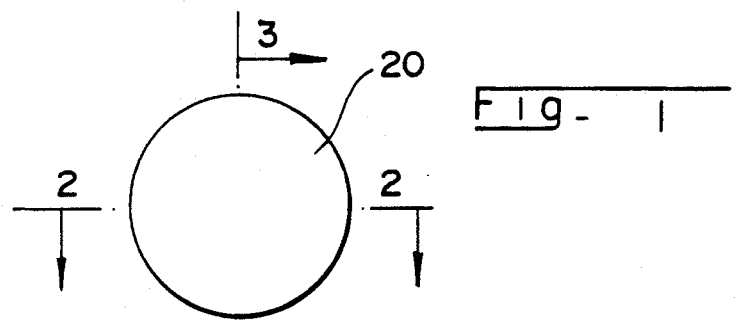
Fig-1
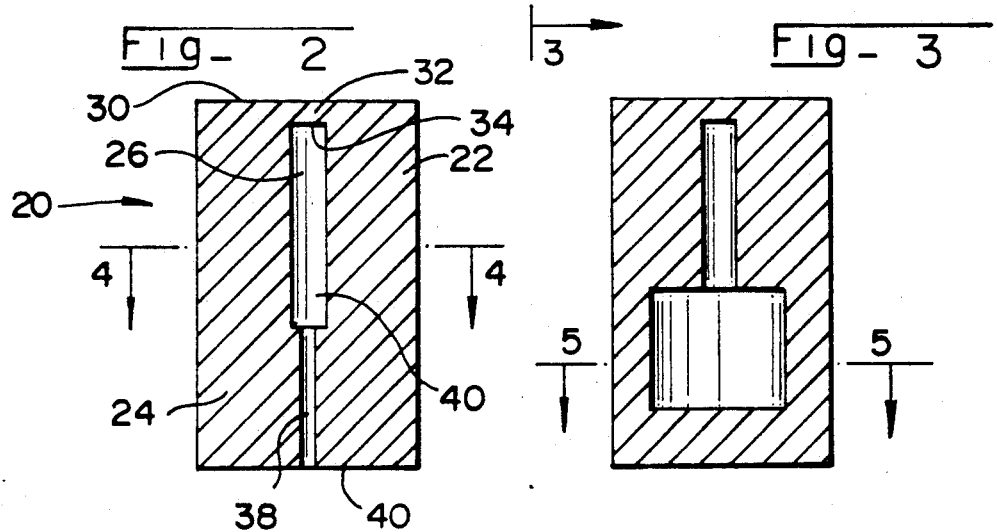
Fig-2        Fig-3
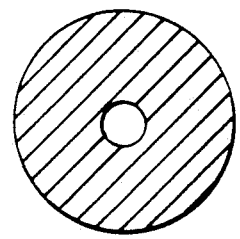   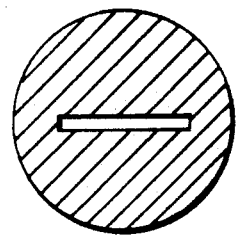
Fig-4        Fig-5
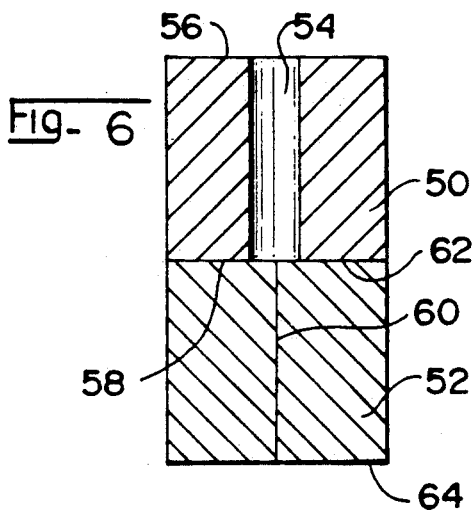   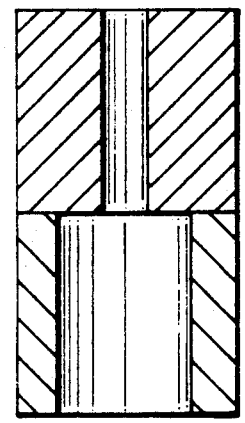
Fig-6        Fig-7

SEPTUM FOR A BLUNT CANNULA

BACKGROUND AND SUMMARY OF THE INVENTION

The invention relates to a septum for coupling intravenous conduits and the like.

The attachment of intravenous tubing to intravascular catheters for the administration of fluids and medication to patients has been widely utilized for decades. Generally, an intravenous tubing system comprises a segment of tubing which is distally attached to an intravascular catheter inserted into a patient's blood vessel. Such primary conduits usually have junction terminals at an end thereof which are occluded by a penetrable septum. A secondary conduit may be connected to the primary conduit system for the administration of fluids into the patient.

One major problem with this kind of system is that the needles frequently loosen and become disconnected from the septum during fluid administration. This can result in the medication spilling into the patient's bed or onto the floor. An even greater problem is that the needle may become contaminated through disconnection. Although inadvisable, nurses may upon occasion readvance a contaminated needle portion through the septum thereby introducing contamination into the primary tubing system.

Yet another problem with existing systems is the danger that the needle poses to health care workers who must daily make numerous connections and disconnections and for whom the contaminated needle represents a major health risk. Inadvertent needle stick has long represented one of the greatest dangers to medical workers. Not only can needle stick occur during connection and disconnection, but needles occasionally become lost in the bed or elsewhere and provide a continual danger to all workers in the hospital environment. The estimated incidence of needle stick injury is 600,000 to 1,000,000 cases per year. Needle sticks tend to occur particularly when a nurse is using many very different types of intravenous conduit systems and is therefore not intuitively familiar with any one system.

Baxter Health Care Corporation is now marketing under the trademark "Needle-Less IV Access System" a connector in which the traditional sharp needle is replaced by a blunt cannula and the traditional solid septum by one having a preperforated slit. The cannula pushes through the slit which to some extent deforms to seal about the cannula. Before insertion, the slit must be sufficiently closed to effectively block passage of fluid, and of course bacteria or other organisms which might move as part of such flow.

An alternative to the blunt cannula is a needle the end of which is pointed and sufficiently sharp to penetrate a septum, but not sharp enough to easily penetrate skin. For such a blunt needle, a perforation rather than a slit may be sufficient to guide the blunt needle through the septum.

One of the problems with such blunt cannulas and needles is that the perforation or slit will not, in every instance, perfectly deform to tightly hug the outer surface of the cannula as a septum does to a sharp needle. This will be more of a problem for some septae than for others because of manufacturing tolerances. To the extent that the slit does not conform exactly to the outside surface of the cannula, passages are created for potential contamination along the outer surface of the cannula in both directions. Moreover, a tendency exists for liquid droplets within the cannula to be thrown off as it is withdrawn from the slit. Further, the possibility exists that sterility will eventually be lost even if the initial seal is acceptable as the slitted septum will often be in ambient for many days while being penetrated by a cannula.

Moreover, with this type of slitted septum a tradeoff exists between the degree of sealing provided by the slit and the force required to insert the cannula. Tighter sealing can be achieved by utilizing material which is more resilient and reducing the width of the slit. However, this approach makes it more difficult for the nurse to insert the cannula or needle. Since a nurse must make such insertion many times each day, ease of insertion is an absolute requirement. Further, in many cases the junction terminal, the catheter, and the blood vessel are in close approximation so that minimum transmission of force to the junction terminal is critical to prevent the transmission of force to the vein through the catheter, which force could damage the vein.

The present invention relates to a unique improved system of the type described above in which a seal provides improved security against passage of contamination without undue force being required to insert the blunt needle or cannula.

In one embodiment, the septum is provided in its upper proximal portion with a bore having substantially the same diameter or a slightly smaller diameter than that of the cannula or needle and a lower distal portion which is a slit similar to that described above. Preferably the bore and cannula have a circular cross section but other shapes may be desirable. The slit also may be other than linear. For example it may be curved. Alternatively, the slit may be in the upper proximal portion and the bore below it in the lower distal portion.

The bore, by conforming very closely to the surface of the cannula or needle reduces the possibility of passage through the septum along the exterior surface of the cannula or needle. The slit at the same time reduces the possibility that the septum will provide any passage before the cannula is inserted since it will close more tightly than the bore when the needle or cannula is not present.

Further, since the bore provides tight sealing around the cannula, the slit need not grip the cannula as tightly as would otherwise be desirable. Thus, the force required for the nurse to push the cannula or needle through the septum can be established at an acceptable and workable level.

According to a further aspect of the invention, the passage in the upper portion of the septum need not extend to the surface when the septum is first provided for use. Rather, a thin unbroken membrane is formed between the end of the passage and the upper proximal surface of the septum. Thus, there is complete and total protection against passage of bacteria or other contaminant until that membrane is first broken by pushing the blunt cannula or needle through the membrane via the passageway in the upper portion of the septum and through the slit in the lower portion.

In a further embodiment, a slit is extended into the septum from both ends, leaving an unbroken portion therebetween. This unbroken portion provides an absolute block to passage of contamination until broken by penetration of a blunt cannula or needle.

Annular rings on the outer surface of the cannula or needle can be provided and spaced apart by the length of the septum, or slightly less than the length to provide a further measure of sealing and to serve as detents.

To assist in insertion and to adjust for different sized cannula and needles, an indentation may be provided extending from the proximal end of the septum toward the distal. The indentation communicates with a slit extending the rest of the way through the septum to the other end. Alternatively, ring-like protrusions are provided on at least one end of the septum about the slit to grip the cannula or needle.

In another disclosed embodiment the septum is provided with a weakened core through which the blunt cannula or needle can penetrate.

Other objects and purposes of the invention will be clear from the following detailed description of the drawings.

BRIEF DESCRIPTION OF THE DRAWINGS

FIG. 1 shows a top view of a first embodiment of the present invention in which the upper surface of the septum is unbroken.

FIG. 2 shows a sectional view of the embodiment of FIG. 1 through the lines 2—2.

FIG. 3 shows a sectional view of the embodiment of FIG. 1 through the lines 3—3.

FIG. 4 shows a sectional view of the embodiment of FIG. 1 through the lines 4—4 of FIG. 2.

FIG. 5 shows a sectional view of the embodiment of FIG. 1 through the lines 5—5 of FIG. 3.

FIG. 6 shows a sectional view of a further embodiment of the invention in which the upper proximal and lower distal portions are formed separately. The section is of a septum as in FIG. 2.

FIG. 7 shows a further sectional view of the further embodiment of FIG. 6 with a section as in FIG. 3.

FIGS. 13(a) and 13(b) are section views and FIG. 13(c) a detailed cross sectional view of one ring-like protrusion.

FIG. 14 is a top plan view.

FIG. 15 is a sectional view and FIG. 16 a top plan view.

DETAILED DESCRIPTION OF THE DRAWINGS

Figure 8:
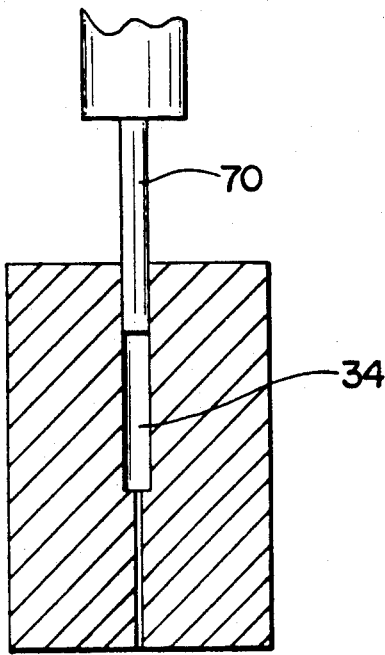
FIG. 8 shows a sectional view of the embodiment of the FIGS. 1-5 with a blunt cannula having penetrated the membrane and pushing into the passageway in the upper portion of the septum.

Reference is now made to FIGS. 1-5 which illustrate a first embodiment of the invention. In this embodiment, an integral septum (20) is provided with an upper proximal section (22) and a lower distal section (24). The upper section here refers to the proximal end of the septum first penetrated by the blunt needle or cannula. Of course, since the septum is integral, no actual boundary or division between the two portions of the septum exists. The septum may be molded or otherwise formed from any suitable elastomeric material.

A cylindrical bore or passageway (26) extends within the upper portion of the septum to a location adjacent the upper surface (30) of the septum which would be the surface distal to the patient and the surface penetrated first by the cannula or needle. Membrane (32) is thus defined between the termination (34) of passageway (26) and upper surface (30). The thickness of such membrane (32) may be between 1 and 10 millimeters and is preferably sufficient to provide secure isolation of passageway (26) from surface (30) while at the same time being penetratable without excessive force by a blunt cannula or needle.

Passageway (26) is coupled to a slit (38) extending from the lower end (40) to passageway (26). Since the septum is of suitable flexible material, the slit (38) is normally closed except when pushed open by passage of a cannula or needle. The circular cross section of passage (26) can be seen in FIG. 4 and the shape of the slit (38) in FIG. 5.

FIGS. 6 and 7 illustrate a further embodiment of the invention in which the upper section (50) and lower section (52) are made of different elastomeric materials, which for example may have different rigidity and flexibility. The two sections are bonded or molded together in a firm and complete bonding so as to avoid any possibility of bacteria or other organisms growing in the space between the upper and lower portions. As in the embodiment of FIGS. 1-5, a bore (54) which is cylindrical in cross section extends from the upper surface (56) of section (50) to the lower surface (58) of section (50) where it communicates with a slit (60) extending from the upper surface (62) of lower section (52) to the lower surface (64) thereof. Slit (60) and bore (54) function as described above.

Figure 9:
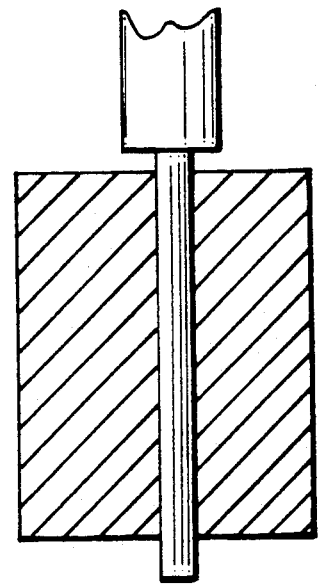
FIG. 9 shows a blunt cannula having penetrated entirely through the septum.

FIGS. 8 and 9 illustrate how a blunt cannula, such as known in the art, penetrates through the membrane separating upper surface (30) into cylindrical passageway (26). As the cannula (70) penetrates through the passageway (26) the walls thereof conform closely to the cylindrical exterior surface of cannula (70). Preferably, the diameter of passageway (26) is just slightly smaller than that of cannula (70) so that the fit is snug and no passage is provided through which bacteria or other micro-organisms can migrate.

As shown in FIG. 9, as cannula (70) then penetrates through the slit (38) in the lower portion, that slit is forced open and conforms, at least to some extent, to the shape of cannula (70). Since it must deform from a slit, however, the gripping of the cannular outer surface by the slit walls cannot be as effective and as tight as the gripping by the walls of the cylindrical bore (26) which conforms exactly to the diameter of the outer surface of cannula (70). However, since the passageway (26) provides a tight fit precluding any passage of contamination along cannula (70), small gaps formed by the slit deformation around the surface of cannula (70) will have no detrimental result.

Figure 10:
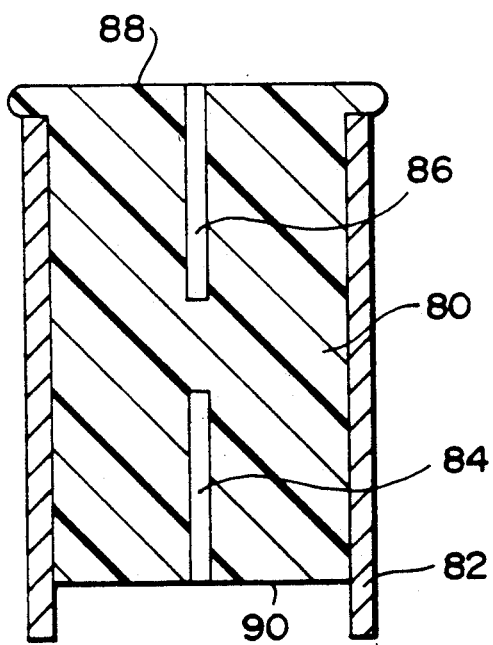
FIG. 10 shows a further embodiment in which the central portion is unbroken.

In FIG. 10, septum (80) which is lodged in housing (82) is provided with respective slits (84) and (86) which extend inwardly from opposite ends (88) and (90). Preferably the septum (80) and housing (82) are joined together by core molding. However, an unbroken portion of septum (80) is maintained between the slits so a secure seal is provided until broken by passage of a needle or blunt cannula. Thus, absolute sterility is maintained until the septum is penetrated.

Figure 11:
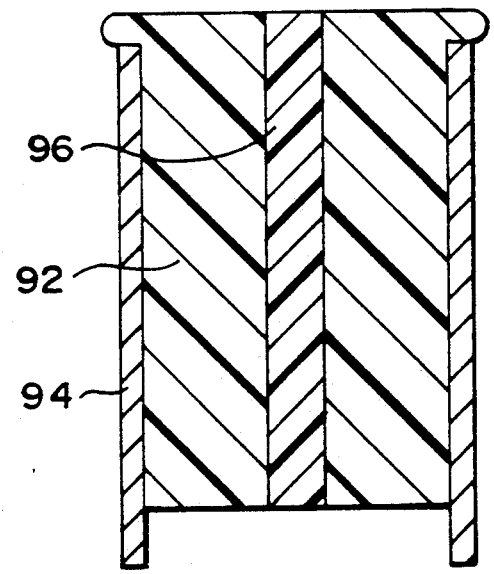
FIG. 11 shows an embodiment with a weakened core.

In FIG. 11, septum (92) in housing (94) is provided with a weakened core (96) of the same or different elastomeric material from the rest of the septum. Because the core is weak, even the blunt cannula may be pushed through, forming a passage as it goes. At the same time, the integrity of the septum is maintained because the rest is formed of strong elastomeric material. It is important that no gap exist between core (96) and the surrounding septum material. One way to achieve this is to employ core molding techniques.

Figure 12:
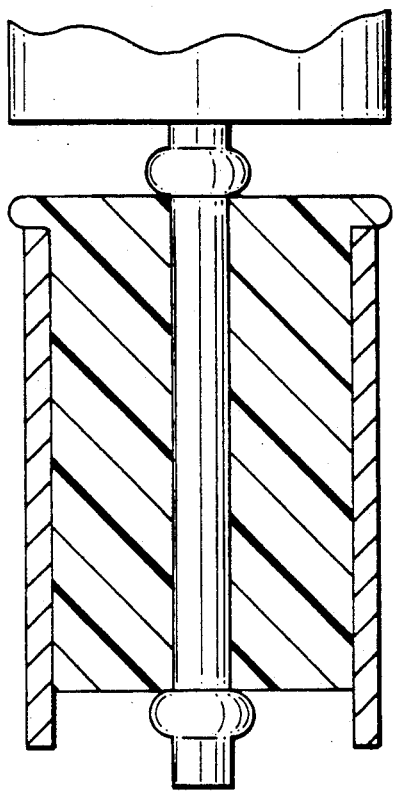
FIG. 12 shows an embodiment in which annular rings are provided on the outer surface of the cannula.

FIG. 12 shows an embodiment in which sealing is improved by virtue of separated and integral annular rings (100) and (102) provided on the outer surface of cannula (104) which extends from, and is removably connected to, syringe (106). The rings (100) and (102) are separated by a distance equal to or slightly less than the length of elastomeric member or septum (108). When the separation is less, septum (108) is slightly compressed and this can aid in sealing as well. In any event, rings (100) and (102) make more difficult passage of any contaminant through septum (108). As above, the septum (106) is provided with a performed slit (110).

Rings (100) and (102) are additionally useful because they provide a tactile indication to the nurse when cannula (104) has fully penetrated the septum (106) and is in the proper position. As such, rings (100) and (102) act as detents. Rings (100) and (102) provide a small measure of protection against inadvertent disconnection as well. If desired, the surfaces of the septum adjacent the slit can be recessed to receive the rings. The ring-like protrusions will also to some extent wipe off droplets at the end of the blunt needle or cannula and minimizing the risk of such droplets contacting a nurse or other worker. Further, the rings guide the nurse in inserting the cannula at the right point for penetration.

Figure 13A:
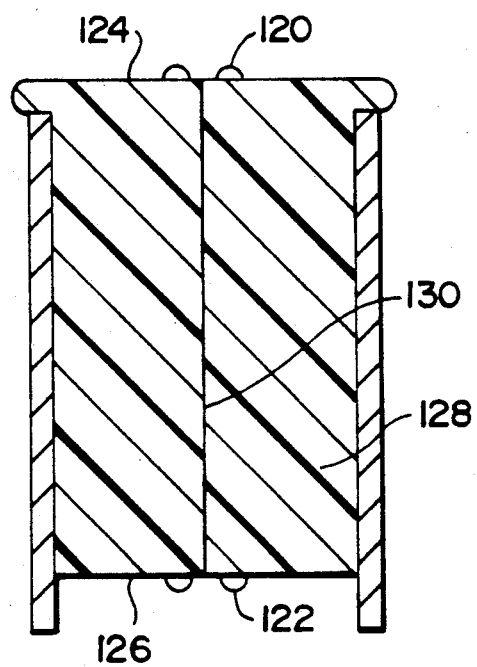
FIGS. 13(a), 13(b), 13(c) and FIG. 14 show an embodiment in which ring-like protrusions are provided on the ends of the septum.
Figure 13B:
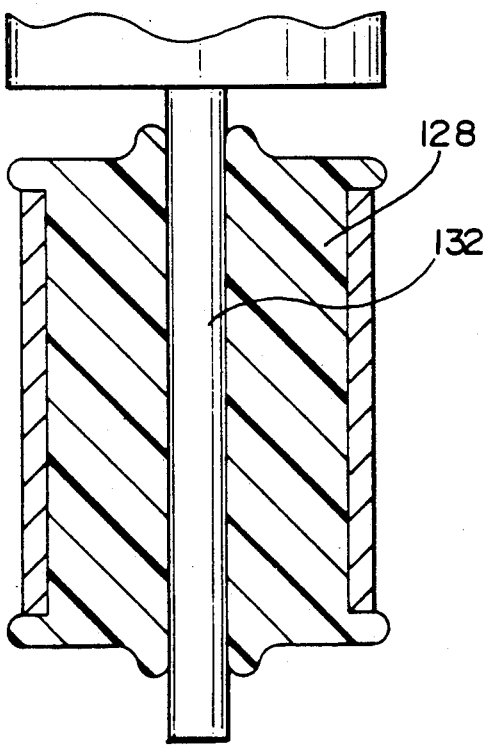
Figure 13C:
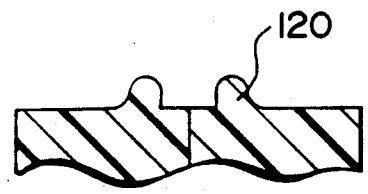
Figure 14:
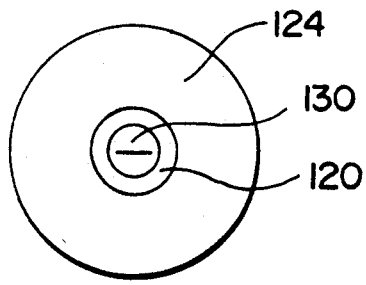

FIGS. 13 and 14 show another embodiment in which improved sealing is effected by providing doughnut shaped protrusions (120) and (122) on the respective proximal and distal ends (124) and (126) of septum (128) and surrounding slit (130). These protrusions grip cannula (132) as it is inserted to provide another barrier to passage of contamination. As shown in FIG. 13(c), the rings preferably extend toward each other in the direction away from the septum. The protrusions guard further against any further tearing of septum (128) as cannula (132) forces passage through slit (130).

Figure 15:
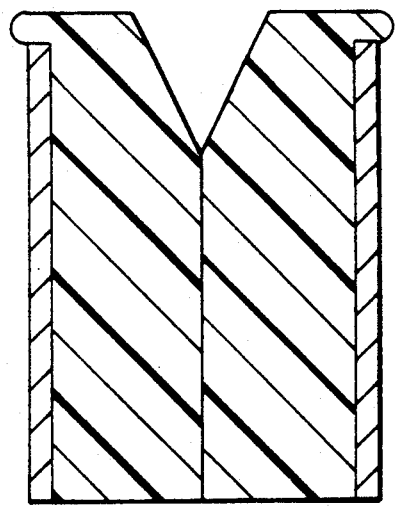
FIGS. 15 and 16 show an embodiment in which a tapering indentation is provided into the proximal end of the septum.
Figure 16:
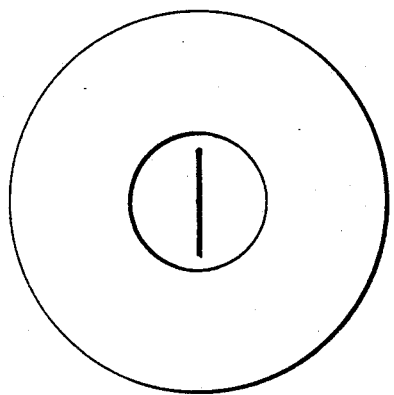

FIGS. 15 and 16 illustrate an embodiment similar to that of FIGS. 1-6 in which slit (150) formed in septum (152) extends from lower surface (154) to terminate in an inwardly tapered indentation (156) extending from proximal end (158) to slit (150). Indentation (156) eases insertion of the blunt needle or cannula by guiding and centering the end thereof onto the opening of the recessed slit (150) through which it can then penetrate. The nurse can readily see the indentation and in fact can find it by feel if necessary. At the same time tapering indentation (156) snugly grips the cannula or needle adjacent the opening of slit (150). Because of the taper, indentation (156) will also grasp cannulas and needles of considerably varying diameters. The indentation preferably has a conical shape and is joined to a housing (160). The housing (160) and septum (152) may be core molded together.

Many changes and modifications can, of course, be carried out without departing from the spirit of the invention. Accordingly, the claims which follow are intended to define the invention.

What is claimed:

1. A homogeneous elastomeric member adapted to occlude and seal a medical terminal, and further adapted to be penetrable by a blunt needle or cannula to establish a fluid communication through said homogeneous elastomeric member, said homogeneous elastomeric member comprising:

a passageway extending only partially through said homogeneous elastomeric member, said passageway including a first portion and a second portion, said first portion of said passageway is defined by a bore adapted to receive said blunt needle or cannula substantially without clearance, and said second portion of said passageway is defined by a plurality of confronting surfaces which, in the absence of penetration by said blunt needle or cannula, abut each other to substantially occlude said passageway; and sealing means for preventing passage of contamination through said homogeneous elastomeric member along said passageway, said sealing means including a portion of said homogeneous elastomeric member adapted to be ruptured by penetration of said blunt needle or cannula.

2. A homogeneous elastomeric member as in claim 1 wherein said sealing means is adjacent an end of said homogeneous elastomeric member.

3. A homogeneous elastomeric member as in claim 1 wherein said first portion of said passageway extends between said second portion of said passageway and said sealing means.

* * * * *